(12) United States Patent
Sugihara et al.

(10) Patent No.: US 7,068,364 B2
(45) Date of Patent: Jun. 27, 2006

(54) PATTERN INSPECTION APPARATUS

(75) Inventors: Shinji Sugihara, Tokyo (JP); Mitsuo Tabata, Yokohama (JP); Hideo Tsuchiya, Kawasaki (JP); Yasushi Sanada, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 207 days.

(21) Appl. No.: 10/627,702

(22) Filed: Jul. 28, 2003

(65) Prior Publication Data
US 2004/0070753 A1    Apr. 15, 2004

(30) Foreign Application Priority Data
Jul. 29, 2002    (JP) .............................. 2002-219878

(51) Int. Cl.
*G01N 21/88* (2006.01)
(52) U.S. Cl. ................................. 356/237.5
(58) Field of Classification Search .. 356/237.1–237.6, 356/388–395
See application file for complete search history.

(56) References Cited

U.S. PATENT DOCUMENTS 5,502,311 A * 3/1996 Imai et al. .................. 250/548

5,995,219 A    11/1999 Tabata

FOREIGN PATENT DOCUMENTS

JP          2000-9656          1/2000

* cited by examiner

Primary Examiner—Tu T. Nguyen
(74) Attorney, Agent, or Firm—Oblon, Spivak, McClelland, Maier & Neustadt, P.C.

(57) ABSTRACT

A pattern inspection apparatus includes a light source irradiating a plate having a pattern, a photoelectric device photoelectrically converting the image of the pattern, a generator generating detected pattern data based on a photoelectrically converted signal, a generator generating reference pattern data from designed data, a comparator comparing the detected pattern data with the reference pattern data, a sensor detecting a light intensity of the light source, a barometric pressure sensor detecting a barometric pressure in the apparatus, a detector detecting at least one of the light intensity and barometric pressure deviating from predetermined ranges, a memory storing the detected and reference pattern data at a point of time when the abnormal status is generated in synchronization with position data and detected values of the light intensity and barometric pressure and an output device which outputs these.

6 Claims, 5 Drawing Sheets

PATTERN INSPECTION APPARATUS

CROSS-REFERENCE TO RELATED APPLICATIONS

This application is based upon and claims the benefit of priority from the prior Japanese Patent Application No. 2002-219878, filed Jul. 29, 2002, the entire contents of which are incorporated herein by reference.

BACKGROUND OF THE INVENTION

1. Field of the Invention

The present invention relates to a pattern inspection technique in which a defect of a circuit pattern formed on a substrate is inspected, particularly to a pattern inspection apparatus in which a defect of a micro pattern formed in a transfer mask for lithography for use in manufacturing a semiconductor device or a liquid crystal display (LCD), or in a semiconductor substrate or liquid crystal substrate is inspected.

2. Description of the Related Art

In recent years, miniaturization of a pattern size of a large scale integrated circuit (LSI) has advanced year by year, and it is expected that products having a minimum line width of 0.1 µm or less will be mass-produced in the near future. With this miniaturization, the dimension of a defect which has to be detected has been remarkably small, and development of a pattern inspection apparatus which inspects pattern defects of a pattern of the LSI and a mask for transfer for use in manufacturing the LSI has become indispensable.

Moreover, with advances in information techniques and multimedia techniques, in LCDs, enlargement of a liquid crystal substrate size and miniaturization of patterns such as thin film transistors formed on a liquid crystal substrate have advanced. Therefore, it has been requested to inspect a broad range for a remarkably small pattern defect. Accordingly, there has been a pressing need to also develop a pattern inspection apparatus which efficiently inspects the pattern defects of a pattern of such a large-area LCD and a photo mask for use in manufacturing the large-area LCD in a short time.

In a conventional pattern inspection apparatus, optics similar to a microscope are used to enlarge the pattern formed on a plate to be inspected of a mask for transfer at a predetermined magnification and to inspect the pattern. That is, the plate to be inspected is laid on a stage, and the pattern formed on the plate is inspected during stage running. The substrate is irradiated with a luminous flux having such a size that the predetermined region of the pattern are covered by an appropriate light source and condensing optics during inspection. The light transmitted through the plate to be inspected is incident upon a photoelectric device via magnification optics, and an optical image of the pattern is formed on the photoelectric device. The optical image of the pattern formed on the photoelectric device is photoelectrically converted, and sent as detected pattern data to a comparison circuit.

On the other hand, designed pattern data of the plate to be inspected is converted into the pixels in a reference pattern data generator, subjected to an appropriate filtering process, and converted to an image equivalent to the optical image. Thereafter, the image is sent as reference pattern data to the comparison circuit. In the comparison circuit, the detected pattern data is compared with the reference pattern data in accordance with an appropriate algorithm. When the data do not agree with each other, it is judged that there is a pattern defect. It is to be noted that when there is a region of repetition of the same pattern in the plate to be inspected, detected pattern data acquired in the photoelectric device for only a given region is stored instead of the designed data, and used as the reference pattern data for comparison. This system is also generally used.

Image data (detected pattern data) of the pattern defect determined as the defect is stored in the data memory of a computer in order to confirm a situation of the defect after the inspection. On the other hand, since the total data amount of the measured image data is enormous, other normal image data is discarded.

However, this type of apparatus has the following problems. That is, since the detected pattern data corresponding to a non-defect after the comparison is discarded, the detected pattern data at an apparatus abnormal status time cannot be analyzed. Therefore, there is a possibility that a cause-effect relation between the abnormal status of the apparatus and the defect inspection becomes obscure. As a result, there is a problem that the apparatus abnormal status influencing an inspection result is missed. Conversely, there is a problem that an unnecessary re-inspection is carried out and throughput is lowered. When the abnormal status is recognized in the apparatus, there is not any means for confirming a pattern comparison situation at this time, and therefore there is also a problem that reliability of the inspection performed in the past cannot be assured.

It is to be noted that when all the detected pattern data is stored in the data memory, the total image data is enormous. Therefore, this is not realistic for the pattern inspection apparatus which is used at a point of mass production and which carries out a large number of inspections throughout the year.

Therefore, there has been a demand for realization of a pattern inspection apparatus which can inspect the defect of the pattern on the plate to be inspected and by which the cause-effect relation between the apparatus abnormal status and the defect inspection can be recognized and which can contribute to enhancement of an apparatus availability and reliability.

BRIEF SUMMARY OF THE INVENTION

According to a first aspect of the present invention, there is provided a pattern inspection apparatus comprising:

a stage on which a plate to be inspected including a pattern formed on the plate is laid;

a light source which irradiates the plate to be inspected with light;

a photoelectric device which photoelectrically converts the optical image of the pattern;

a detected pattern data generator which generates detected pattern data regarding the pattern based on a signal obtained by the photoelectric device;

a reference pattern data generator which generates reference pattern data from designed data regarding the pattern, or stores the detected pattern data obtained by the photoelectric device;

a comparator which compares the detected pattern data with the reference pattern data;

a light intensity sensor which detects a light intensity of the light;

a barometric pressure sensor which detects a barometric pressure in the pattern inspection apparatus;

a status detector which senses that at least one of the light intensity and the barometric pressure deviates from a predetermined range;

a data memory in which the detected pattern data and the reference pattern data regarding the detected pattern data at the same time as a time when the status detector detects that the at least one of the light intensity and the barometric pressure deviate from the predetermined ranges are stored in synchronization with position data on the plate to be inspected and a detected value of the at least one of the light intensity and the barometric pressure deviating from the predetermined range; and an output device which outputs the detected pattern data, the reference pattern data, and the detected value of the at least one of the light intensity and the barometric pressure stored in the data memory.

According to a second aspect of the present invention, there is provided a pattern inspection apparatus comprising:

a stage on which a plate to be inspected including a pattern formed on the plate is laid;

an electron gun which generates electron beams;

an electron optics which irradiates the plate to be inspected with the electron beams;

a secondary electron detector which detects secondary electrons generated from the plate to be inspected;

a detected pattern data generator which generates detected pattern data regarding the pattern based on a signal obtained by the secondary electron detector;

a reference pattern data generator which generates reference pattern data from designed data concerning the pattern, or stores the detected pattern data obtained by the photoelectric device;

a comparator which compares the detected pattern data with the reference pattern data;

a dose sensor which detects a dose of the electron beams;

a barometric pressure sensor which detects a barometric pressure in the pattern inspection apparatus;

a status detector which detects that at least one of the dose of the electron beams and the barometric pressure deviates from a predetermined range;

a data memory in which the detected pattern data and the reference pattern data regarding the detected pattern data at the same time as a time when the status detector detects that the at least one of the dose of the electron beams and the barometric pressure deviates from the predetermined range are stored in synchronization with position data on the plate to be inspected and the detected value of the at least one of the dose of the electron beams and the barometric pressure deviating from the predetermined range; and an output device which outputs the detected pattern data, the reference pattern data, and the detected value of the at least one of the dose of the electron beams and the barometric pressure stored in the data memory.

BRIEF DESCRIPTION OF THE SEVERAL VIEWS OF THE DRAWING

FIG. 4A shows one example of a normal image, and FIG. 4B shows one example of the image at a defocus time;

FIG. 7A is a diagram of the image in the case in which a stage vibrates in a diagonal direction, and FIG. 7B is a diagram showing predetermined places for performing a gradient analysis.

DETAILED DESCRIPTION OF THE INVENTION

Embodiments of the present invention will be described hereinafter.

(First Embodiment)

Figure 1:
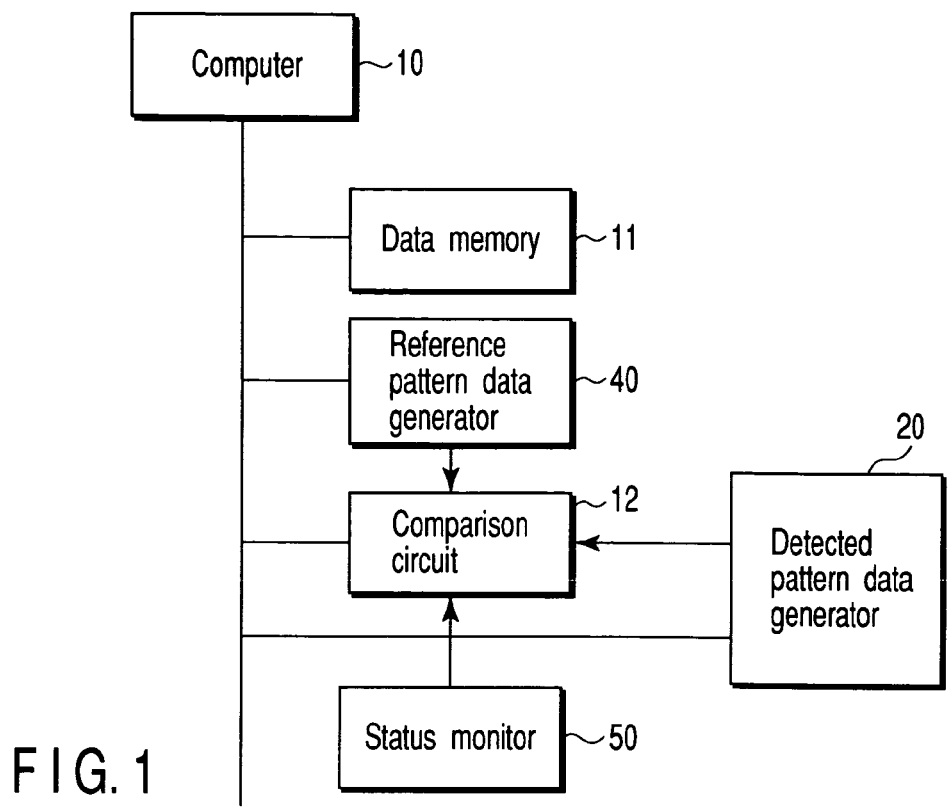
FIG. 1 is a block diagram showing a basic configuration of a pattern inspection apparatus according to a first embodiment.

FIG. 1 is a block diagram showing a basic configuration of a pattern inspection apparatus according to a first embodiment of the present invention. The pattern inspection apparatus of the present embodiment has a basic configuration including: a computer 10; an inspection data generator 20 for generating detected pattern data corresponding to a pattern of a plate to be inspected (mask for exposure); a reference pattern data generator 40 for generating reference pattern data as an inspection standard from designed data; a status monitor 50 for monitoring the state of each part of the apparatus; a comparison circuit 12 for comparing the detected pattern data with the reference pattern data; and a data memory 11 in which the designed data and image data are stored.

Figure 2:
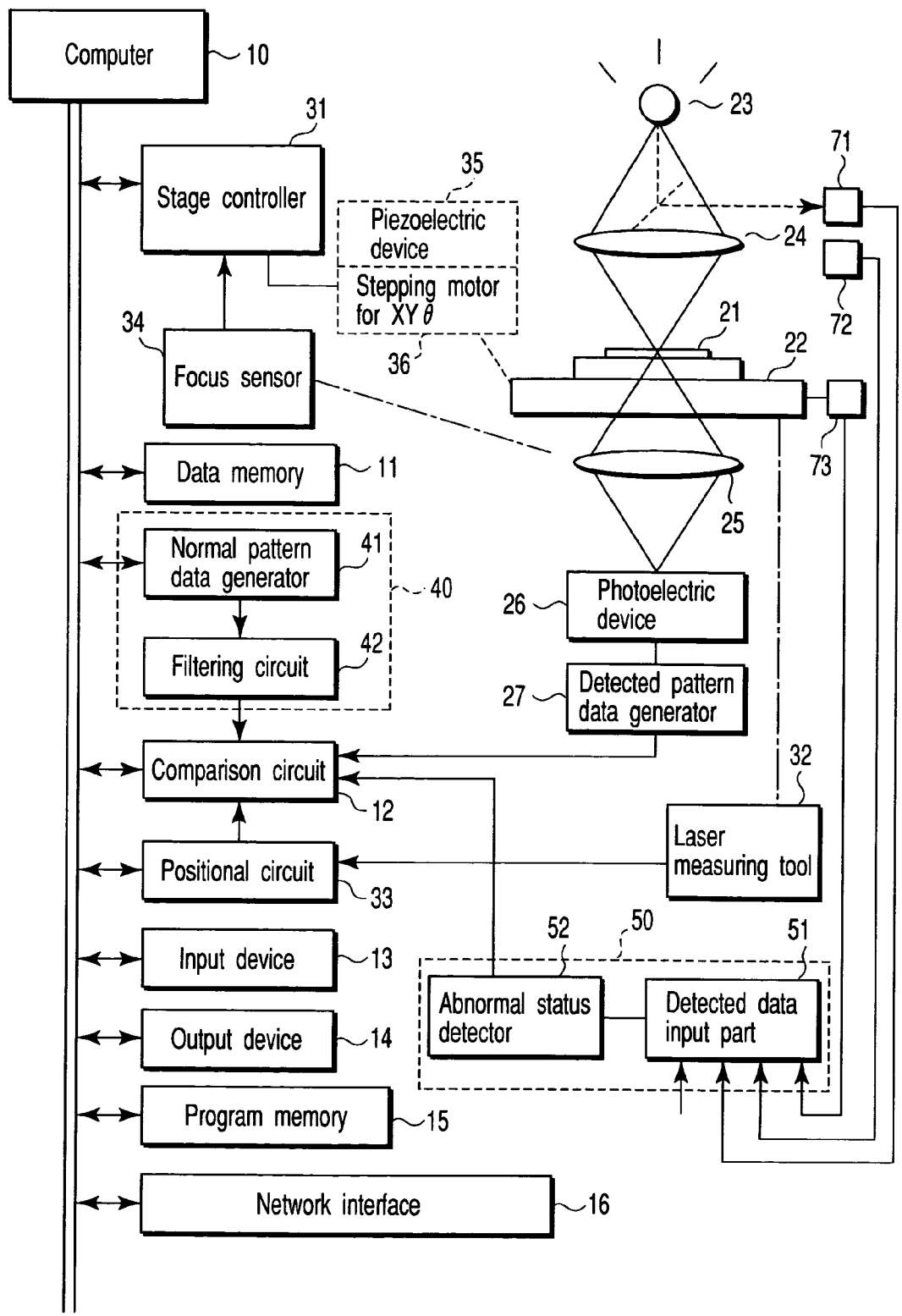
FIG. 2 is a diagram showing the whole configuration of the pattern inspection apparatus of the first embodiment.

FIG. 2 is a diagram showing the whole configuration of the pattern inspection apparatus of the present embodiment. The inspection data generator 20 includes: a stage 22 for mounting the plate to be inspected; a light source 23; illumination optics 24; magnification optics 25; a photoelectric device 26; a detected pattern data generator 27; a stage controller 31; a laser measuring tool 32; a positional circuit 33; and a focus sensor 34.

Moreover, the reference pattern data generator 40 includes a normal pattern data generator 41 and filtering circuit 42. Furthermore, the status monitor 50 includes a detected data input part 51 and abnormal status detector 52.

A plate to be inspected 21 such as the mask for exposure is automatically supplied onto the stage 22 for the plate to be inspected by an auto loader mechanism, and is automatically discharged after end of inspection. The illumination optics 24 including the light source 23 and a condensing lens are disposed above the stage 22. The plate to be inspected 21 is irradiated with light from the light source 23 via the illumination optics 24. The magnification optics 25 and photoelectric device 26 are disposed under the plate to be inspected 21. Moreover, a light receiving surface of the photoelectric device 26 is irradiated with the transmitted light transmitted through the plate to be inspected 21 via the magnification optics 25 so that an image is formed.

The stage 22 for the plate to be inspected is a three-axis (X-Y-θ) manipulator which can move in X and Y directions and can further rotate in a θ direction by the stage controller 31 which has received a command from the computer 10. Moreover, stepping motors 36 are disposed in the X, Y, and θ directions, and the stage is controlled by driving these motors 36. Positional coordinates of the stage 22 are measured by the laser measuring tool 32, and an output is sent to the positional circuit 33. The positional coordinates output from the positional circuit 33 are fed back to the stage controller 31. In the focus sensor 34, a shift amount of the plate to be inspected 21 in a Z-direction from a focus position is measured and sent to the stage controller 31. Moreover, the stage controller 31 controls the piezoelectric device 35 to adjust a Z-direction height of the stage 22 so that the focus shift amount is 0.

A photodiode array for use in the photoelectric device 26 is a line sensor or area sensor in which a plurality of optical sensors are arranged. When the stage 22 is continuously moved in the X-axis direction, a measurement signal corresponding to a pattern to be inspected of the plate to be inspected 21 is detected. The measurement signal is converted to digital data in the detected pattern data generator 27, aligned, and subsequently sent as the detected pattern data to the comparison circuit 12.

The detected pattern data is, for example, unsigned 8-bit data, and represents brightness of each pixel. The detected pattern data is read from the photoelectric device 26 in synchronization with a clock frequency, appropriately rearranged, and handled as two-dimensional raster-scanned image data. Moreover, the data is temporarily stored in a latch memory in the comparison circuit 12. It is to be noted that a buffer memory is disposed between the detected pattern data generator 27 and comparison circuit 12, and the detected pattern data may temporarily be stored in this buffer memory.

The reference pattern data generator 40 sends the designed data read from the data memory 11 to the normal pattern data generator 41, and the normal pattern data generator 41 converts the designed data to pixel data. The pixel data is sent to the filtering circuit 42, and converted to image data (reference pattern data) which has the same quality as that of an image acquired by the optics.

The comparison circuit 12 takes in the detected pattern data generated by the inspection data generator 20 and the reference pattern data having the same coordinates generated by the reference pattern data generator 40, adjusts the positions of these data, subsequently compares the data with each other according to a plurality of algorithms, and judges the data to be defective, when a predetermined significant difference is recognized. In the comparison circuit 12, only the data judged to be defective is stored in the data memory 11, and the data of a normal pattern without any defect is discarded. This is because a pattern pixel size is micro, the size of the plate to be inspected is relatively large, and the total image data handled in one inspection is enormous.

The status monitor 50 includes: the detected data input part 51 for acquiring data indicating an apparatus state in each part of the apparatus; and the abnormal status detector 52 for detecting whether or not the acquired data is in an allowable range. The data acquired by the detected data input part 51 is sent to the abnormal status detector 52. The abnormal status detector 52 uses a comparator circuit to judge the abnormal status in real time. Moreover, when the abnormal status is detected, the monitor 50 sends an apparatus abnormal status signal to the comparison circuit 12.

On receiving the apparatus abnormal status signal, the comparison circuit 12 stores the detected pattern data and reference pattern data in the data memory 11 together with the positional coordinates on the stage 22 for the plate to be inspected, the type of the abnormal status, and parameters regardless of a result of a usual defect detection process. The circuit has a function of: storing the pattern data the predetermined number of times, when the same type of abnormal status is detected the predetermined number of times in a given time; and stopping the image storage with respect to the same type of abnormal status until a predetermined time elapses.

In principle, a period of abnormal status detection is of the same degree as a take-in period of the inspection data generator 20. However, a state having a long time constant of changes such as barometric pressure and temperature can be monitored in a predetermined period longer than that of the inspection data generator 20. At an abnormal status detection time, the pattern data may also be stored the predetermined number of times and at a predetermined time interval. In this case, the abnormal status detector can execute processing with software. Details of monitor items will be described later.

Moreover, the pattern inspection apparatus of the present embodiment has a function of displaying the stored pattern data at the abnormal status time, the type of the abnormal status, or the parameter to an apparatus user. Accordingly, the user can evaluate a degree of influence of the detected apparatus abnormal status onto the inspection based on quality of the acquired image. This display function may also be set to be common with that of an interface for confirmation of an inspection result, which is generally disposed in the pattern inspection apparatus.

Furthermore, the pattern inspection apparatus of the present embodiment includes an input device 13 for accepting inputs of data and command from an operator, an output device 14 for outputting the inspection result, a program memory 15, and a network interface 16. The input device 13 includes a keyboard, mouse, write pen, or floppy disk drive. The output device 14 includes a display device or printer device.

Additionally, in the pattern inspection apparatus of the present embodiment, the following functions are mounted as an apparatus abnormal status monitor system.

(1) Light Amount

A beam splitter is disposed in the illumination optics 24 for irradiating the plate to be inspected with the light, and the light amount is measured by a light intensity measuring device 72 such as a calorie meter. When the light amount deviates from the predetermined range, the abnormal status is judged. A method of measuring an electronic current value of the light source 23 and judging the abnormal status when the value deviates from the predetermined range can also be used.

(2) Stage Vibration

A stage position signal sent from the laser measuring tool 32 is transmitted to the detected data input part 51. In the abnormal status detector 52, a stage positional fluctuation amount per unit time is measured in real time, and the abnormal status is regarded, when the fluctuation amount indicates a predetermined or more value. Moreover, a method of disposing an accelerometer 73 in the stage 22, measuring a stage acceleration during the acquiring of the image, and detecting the abnormal status, when the acceleration exceeds a predetermined value can also be used. Instead of the accelerometer, a vibration sensor 73 may also be disposed.

(3) Focus Abnormal State

The detection of focus abnormal state is monitored by an output of the focus sensor 34. When a Z-direction displacement of the stage 22 per unit time exceeds a predetermined value, the abnormal status is detected. A driving voltage of the piezoelectric device 35 for performing Z-axis driving of the stage 22 can be monitored in real time. When a piezoelectric device driving voltage change per unit time exceeds a predetermined value, the focus abnormal state is judged.

(4) Atmosphere Data

Data of temperature, barometric pressure, and humidity in an apparatus housing in which the stage 22 and optics are contained is measured by the air sensor 72. When the temperature or humidity deviates from a constant range, the abnormal status is determined. When a change ratio of the barometric pressure in the unit time exceeds a given value, the abnormal status is determined.

Here, the influence of barometric pressure fluctuation appears as an offset fluctuation of an auto focus optics, and an apparent optical path length fluctuation of a laser interferometer for detecting a stage position (included in the laser measuring tool 32). The auto focus offset fluctuation is a cause for defocus, the optical path length fluctuation of the laser interferometer is a cause for a reference-sensor image positional shift, and either cause inhibits an inspection accuracy. When the profile of the image is analyzed, two modes can be distinguished, and it is possible to localize trouble. In this respect, it could be understood that it is effective to store the image.

For example, the profile of the image is analyzed based on the detected pattern data in which the image is stored, the defocus or positional shift by the barometric pressure fluctuation is detected, and a correction value is given to the auto focus optics or laser interferometer for the stage so as to correct the defocus or shift. Accordingly, it is possible to perform the inspection while compensating for the influence of the barometric pressure fluctuation. That is, the image stored data can effectively be used in maintenance of the apparatus.

(5) In Addition to the Above-Described States, it is Possible to use Various Apparatus States as Management Items In this manner, according to the present embodiment, in addition to the normal pattern defect inspection, the status monitor 50 is disposed to detect the irradiation amount of the light, the barometric pressure of an installation space of the plate to be inspected, the focus abnormal state, and the vibration of the stage for the plate to be inspected as the apparatus states. When the abnormal status is detected, the detected pattern data and reference pattern data are stored in the data memory 11 together with apparatus abnormal status data. Therefore, it is possible to analyze the pattern image at the apparatus abnormal status time based on each stored data, and the influence of the detected apparatus abnormal status onto the pattern inspection can be evaluated. As a result, it is possible to reduce the missing of the apparatus abnormal status which seriously influences the inspection.

Moreover, since the pattern defects are detected regardless of the presence/absence of the apparatus abnormal status, it is possible to judge whether the detected pattern defect is a real defect or a false defect by the apparatus abnormal status. Furthermore, when the detected pattern data at the apparatus abnormal status time is stored together with apparatus history, it is possible to verify the reliability of the inspection result tracing back to the past.

It is to be noted that in the present embodiment, the transmitted light is used in the illumination optics, but the light allowed to be incident upon the photoelectric device of the inspection data generator is not limited to the transmitted light. A reflected light may also be used, and further both the transmitted light and the reflected light may simultaneously be used. A configuration of the apparatus using the reflected light is not especially shown, but a known technique can be used.

Moreover, the photoelectric device is not limited to a single converter, and a plurality of converters can be used.

(Second Embodiment)

Figure 3:
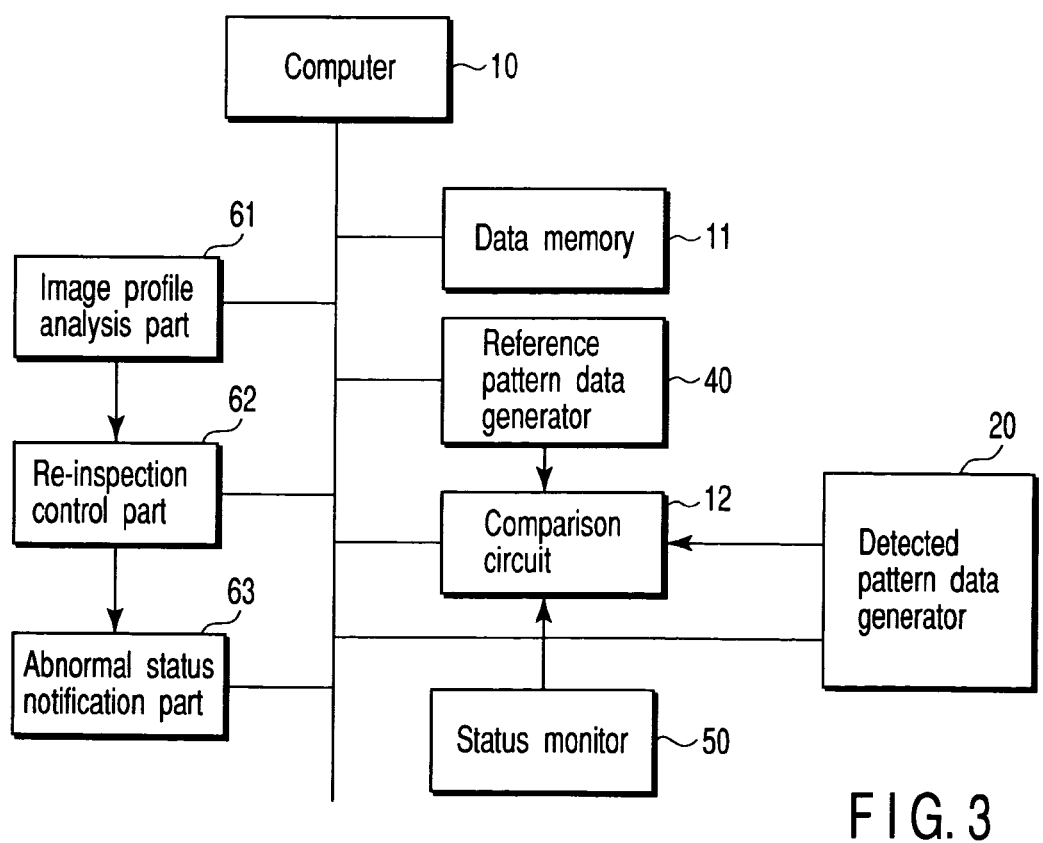
FIG. 3 is a block diagram showing the basic configuration of the pattern inspection apparatus according to a second embodiment.

FIG. 3 is a block diagram showing the basic configuration of the pattern inspection apparatus according to a second embodiment of the present invention. It is to be noted that the same part as that of FIG. 1 is denoted with the same reference numerals, and detailed description is omitted.

In the present embodiment, in addition to the function of the pattern inspection apparatus described in the first embodiment, the apparatus includes an image profile analysis part 61, re-inspection control part 62, and abnormal status notification part 63.

The image profile analysis part 61 analyzes a two-dimensional profile of the detected pattern data stored simultaneously with the detection apparatus abnormal status as described above, and judges necessity of re-inspection based on a predetermined standard determined for each type of the apparatus abnormal status or inspection condition set for each inspection.

On receiving a command from the analysis part 61, the re-inspection control part 62 re-inspects a region including coordinates in which the abnormal status is generated. The range of the re-inspection region is determined by the predetermined standard determined for each type of the apparatus abnormal status, and the inspection condition set for each inspection. Alternatively, the apparatus user can judge the range on the spot.

The abnormal status notification part 63 notifies the apparatus user or an apparatus manager in accordance with the analysis result. A message sending object or message content is determined by the predetermined standard determined for each type of the apparatus abnormal status, and the inspection condition set for each inspection.

As main means of notification in the predetermined apparatus, a message window is displayed on an operation display, and an e-mail is transmitted to notify the apparatus manager. As other notification means, it is possible to use a character output to a console, a printer output, a warning lamp display of a signal tower, a sound message, a warning sound, an output to an inspection result file, an internet messenger, a pager, HTML file update of a WEB server, database update, and the like.

As described above, according to the present embodiment, needless to say, an effect similar to that of the first embodiment is obtained. Additionally, since the image profile analysis part 61, re-inspection control part 62, and abnormal status notification part 63 are disposed, the following effect is obtained. That is, when the abnormal status of the apparatus is detected, the detected pattern data is analyzed, and the re-inspection can be carried out based on the analysis result. Therefore, throughput drop of the inspection is minimized, and the reliability of the inspection can be enhanced. Furthermore, since the apparatus manager or user is quickly notified of the generation of the apparatus abnormal status, it is possible to quickly perform an apparatus maintenance.

(Third Embodiment)

Next, the pattern inspection apparatus according to a third embodiment of the present invention will be described. This embodiment further embodies the second embodiment, and the basic configuration is similar to that of FIG. 3. Items not especially mentioned here conform to those of the first and second embodiments.

Figures 4A, 4B:
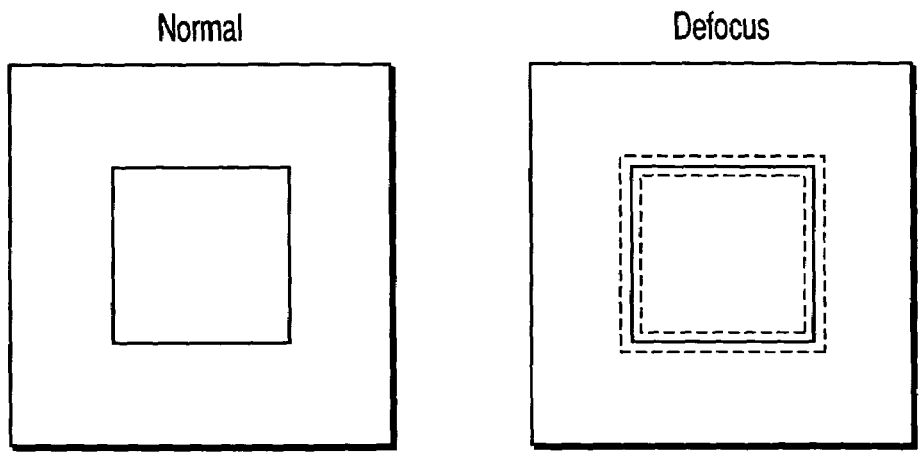
FIGS. 4A and 4B show a focus abnormal state according to a third embodiment.
Figure 5:
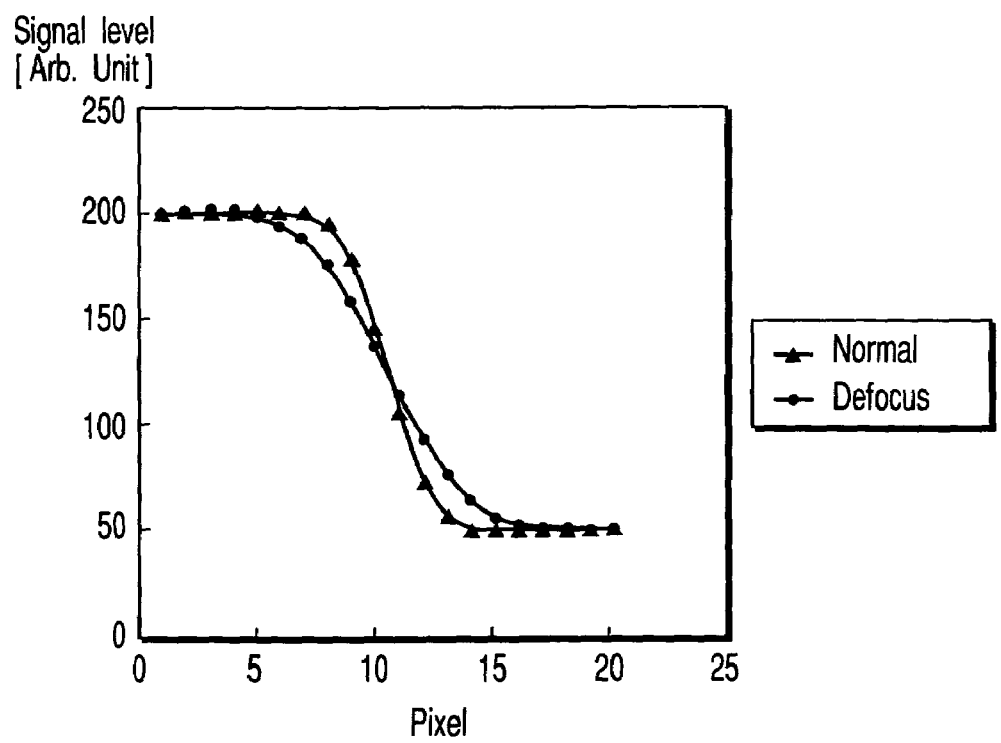
FIG. 5 is a graph showing signal intensity profiles of horizontal-direction pixels in the vicinity of pattern edges of image data in FIGS. 4A and 4B.

The image profile analysis part 61 shown in FIG. 3 analyzes the profile of the pattern edge of the two-dimensional image data. An appropriate image recognition algorithm is used in the detection of the pattern edge. FIGS. 4A and 4B show one example of the image data corresponding to the detected pattern data stored in the data memory 11. FIG. 4A shows the image data at a normal time, and FIG. 4B shows the image data at a defocus time. FIG. 5 shows signal intensity profiles of horizontal-direction pixels in the vicinity of the pattern edges of these image data. As seen from FIG. 5, when the optics maintains a correct focus distance from the plate to be inspected, the gradient of the signal intensity profile of the pattern edge part is steep, but becomes moderate at the defocus time.

Figure 6:
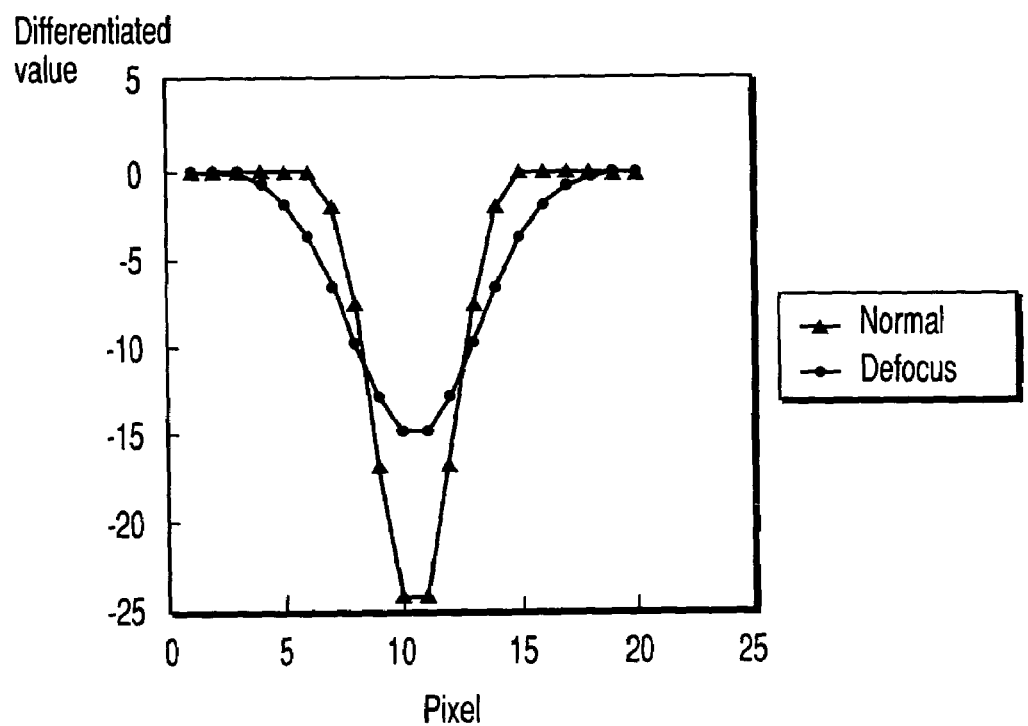
FIG. 6 is a graph showing differential values of the signal intensity profiles of FIG. 5.

FIG. 6 shows differential values of the signal intensity profiles obtained in FIG. 5. In FIG. 6, a maximum differential value at the normal time is about −24, but is about −15 at the defocus time. In this case, a case in which an absolute value of the differentiated value is below 20 is defined as the abnormal status. A threshold value of the differential value depends on the type of the mask, optics, or photoelectric device, and may therefore be set to an appropriate value in accordance with situations.

Moreover, an amplitude or fluctuation of a signal bright part similarly brings a negative influence onto defect detection sensitivity. Therefore, when the bright part of a given region exists in the pattern image corresponding to the detected pattern data stored in the data memory 11, signal intensity and intensity distribution are obtained. When the predetermined range is exceeded, the part is used as an object of the re-inspection. The threshold value of the intensity distribution differs with the type of the mask or the inspection algorithm, but is set to about ±5% in a normal range.

Furthermore, when the image is deteriorated by the vibration of the stage 22, different from the defocus time, a gradient change of the image profile is anisotropically generated. Therefore, to distinguish the defocus from the vibration, the gradients of the profiles in the pattern edges in a longitudinal/lateral direction of the image are compared with each other. When there is a difference between the longitudinal and lateral gradients, stage vibration can be judged. When the gradients are substantially equal to each other, it can be judged that a possibility of defocus is high.

Figure 7A:
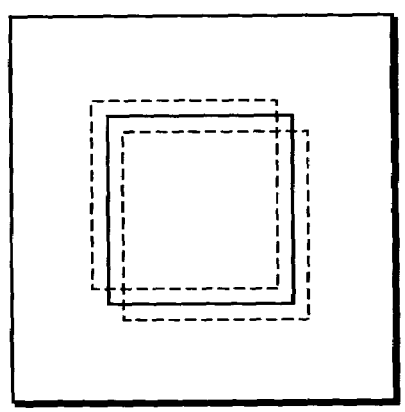
FIGS. 7A and 7B show the focus abnormal state of the third embodiment.
Figure 7B:
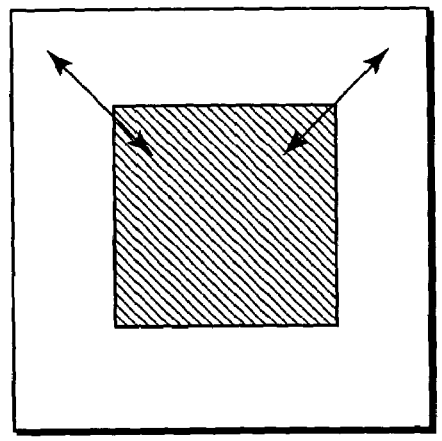

However, when the stage vibrates in a diagonal direction as shown in FIG. 7A, the gradients in horizontal and vertical directions are the same, and it is not easy to distinguish the vibration from the defocus. In this case, when corner parts different in direction exist in the image data as shown in FIG. 7B, the different gradients (directions of arrows) of the corner parts in the diagonal direction are compared with each other. In the case of vibration, since a difference is generated between the gradients, the vibration can be distinguished from the defocus.

It is to be noted that a case in which the stored pattern image is a blank region including no pattern, or a case in which a sufficient pattern for analysis does not exist is also considered. In this case, it is difficult to analyze the signal intensity profile. Therefore, in this case, it is preferable to perform the re-inspection.

As described above, according to the present embodiment, the gradient of the signal intensity profile in the horizontal and vertical directions of the pattern edge part corresponding to the detected pattern data, and the intensity and fluctuation of the signal of the pattern bright part are compared with predetermined standard values. Accordingly, the signal intensity profile of the detected pattern data can be analyzed. As a result, in the same manner as in the second embodiment, the throughput drop of the inspection is minimized, and the reliability of the inspection can be enhanced.

(Fourth Embodiment)

In the first embodiment, the pattern inspection apparatus using the light has been described as the example, but the present invention can also be applied to a pattern inspection apparatus using electron beams.

Figure 8:
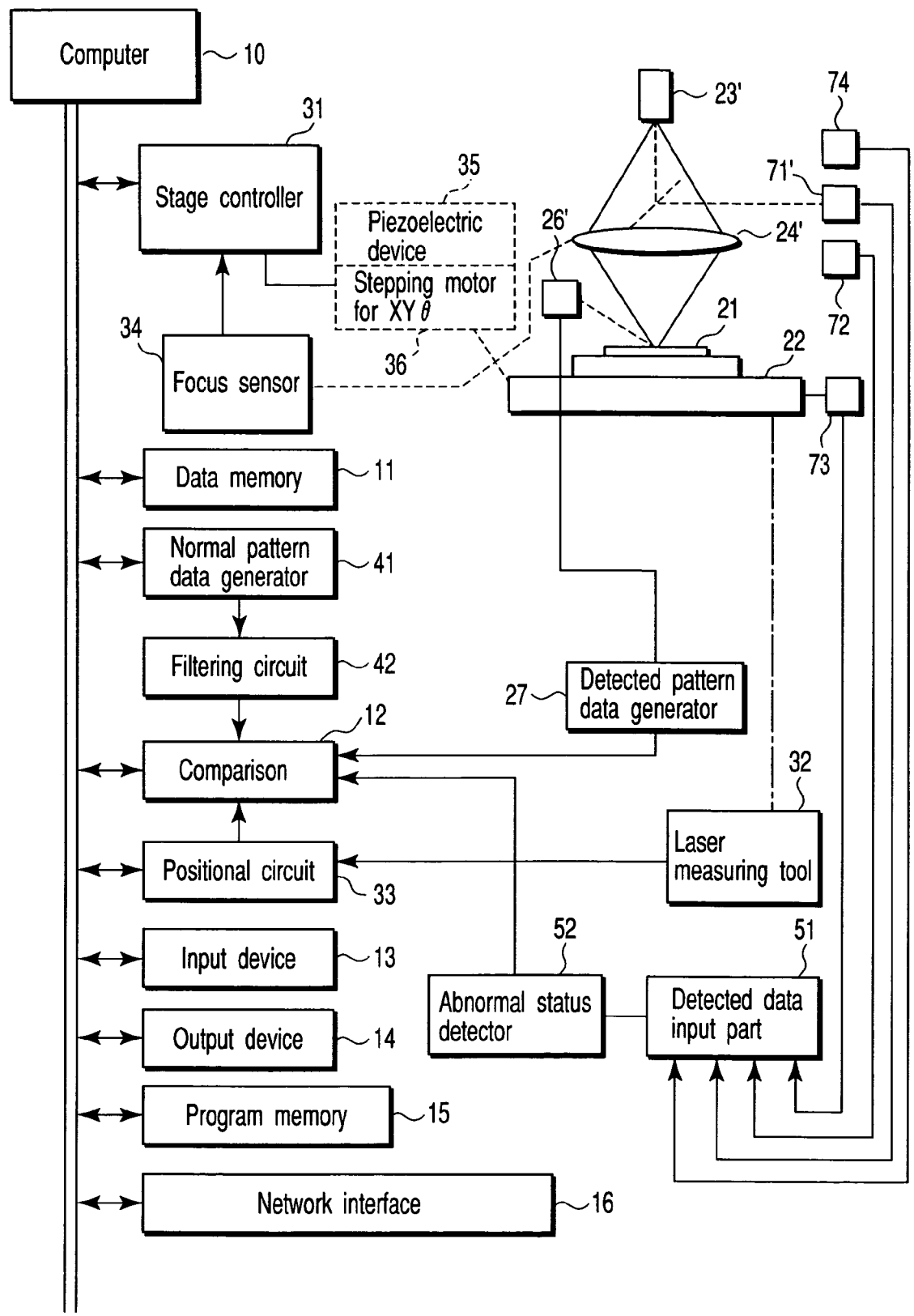
FIG. 8 is a diagram showing the whole configuration of the pattern inspection apparatus of a fourth embodiment.

FIG. 8 is a whole diagram showing the pattern inspection apparatus according to a fourth embodiment, and is different from FIG. 2 only in the optics of the inspection data generator 20. In the present embodiment, an electron gun 23' is disposed instead of the light source 23, and an electron optics 24' is disposed instead of the illumination optics 24. In this apparatus, since secondary electrons from the surface of the plate to be inspected are detected, an electron beam detector 26' is disposed above, for example, obliquely above the plate to be inspected. The electron beam detector is not limited to a single detector, and a plurality of detectors can be used.

Even when this optics is used, the status monitor 50 of FIG. 1 of the first embodiment, or the image profile analyzer of the third embodiment is disposed, and therefore the similar effect can be obtained.

Furthermore, when a magnetic field sensor is disposed as shown in FIG. 8, a magnetic fluctuation which influences the electron beams can be monitored.

MODIFICATION EXAMPLES

It is to be noted that the present invention is not limited to the above-described embodiments. In the embodiments, as the apparatus states, the light amount (irradiation amount), stage vibration, focus abnormal status, and atmospheric state (especially the barometric pressure) are detected. However, the light amount and barometric pressure exert a largest influence on the pattern defect inspection. Therefore, at least the irradiation amount and barometric pressure may be inspected.

Moreover, the reference pattern data is not necessarily limited to data obtained by developing the designed data. For the plate to be inspected which has a region including the repetition of the same pattern, the detected pattern data obtained by the inspection data generator is temporarily held. Accordingly, the data can be used as the reference pattern data with respect to the inspection of the same pattern region disposed in another coordinate on the same mask.

Furthermore, in the embodiments, at the apparatus abnormal status time, the reference pattern data is also stored together with the detected pattern data, but the reference pattern data can be prepared from the designed data. Therefore, the data does not necessarily have to be stored together with the detected pattern data. Additionally, it is preferable to simultaneously store the data in order to analyze a cause-effect relation between the apparatus abnormal status and the defect inspection. Furthermore, when the reference pattern data is prepared from the detected pattern data, not from the designed data, it is essential to simultaneously store the detected pattern data and reference pattern data.

Moreover, the devices for measuring the apparatus state are not limited to the above-described items. A device which can measure the apparatus state in an appropriate period and accuracy can freely be selected. The object to be monitored is not limited to the above-described items.

Furthermore, the plate to be inspected is not necessarily limited to a photo mask, and the present invention can also be applied to the defect inspection of a micro pattern formed in a semiconductor substrate or a liquid crystal substrate.

As described above in detail, according to the present invention, when the abnormal status of the apparatus is detected, the detected pattern data corresponding to a non-defect pattern heretofore discarded is stored together with the apparatus information. Accordingly, it is possible to analyze the pattern image at the apparatus abnormal status time, which has not heretofore been verified. The influence of the detected apparatus abnormal status on the pattern inspection can be evaluated. As a result, the missing of the abnormal status of the apparatus, which seriously influences the inspection, can be reduced. When the detected pattern data at the apparatus abnormal status time is stored in storage means together with the apparatus history, the reliability of the inspection result can be verified tracing back to the past.

Moreover, when the abnormal status of the apparatus is detected, the detected pattern data at this time is analyzed, and the re-inspection is performed based on the analysis result, so that the throughput drop of the inspection can be minimized, and the reliability of the inspection can be enhanced. Furthermore, when the apparatus manager or user is quickly notified of the generation of the apparatus abnormal status, it is possible to quickly perform the apparatus maintenance.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
    a stage on which a plate to be inspected including a pattern formed on the plate is laid;
    a light source which irradiates the plate to be inspected with light;
    a photoelectric device which photoelectrically converts the optical image of the pattern;
    a detected pattern data generator which generates detected pattern data regarding the pattern based on a signal obtained by the photoelectric device;
    a reference pattern data generator which generates reference pattern data from designed data regarding the pattern, or stores the detected pattern data obtained by the photoelectric device;
    a comparator which compares the detected pattern data with the reference pattern data;
    a light intensity sensor which detects a light intensity of the light source;
    a barometric pressure sensor which detects a barometric pressure in the pattern inspection apparatus;
    a status detector which senses that at least one of the light intensity and the barometric pressure deviates from a predetermined range;
    a data memory which stores the detected pattern data and the reference pattern data corresponding to the detected pattern data at a point of time when the status detector detects that the at least one of the light intensity and the barometric pressure deviate from the predetermined ranges in synchronization with position data on the plate to be inspected and a detected value of the at least one of the light intensity and the barometric pressure deviating from the predetermined range;
    an output device which outputs the detected pattern data, the reference pattern data, and the detected value of the at least one of the light intensity and the barometric pressure stored in the data memory;
    a signal intensity profile analysis part which analyzes a signal intensity profile of the detected pattern data at an abnormal status time;
    a re-inspection control part which re-inspects at least a part on the plate to be inspected based on an analysis result of the signal intensity profile analysis part; and
    an abnormal status notification part which notifies the analysis result,
    wherein the signal intensity profile analysis part compares signal gradients of horizontal and vertical direction components of a pattern edge part of the detected pattern data with a first predetermined standard value, and an intensity and fluctuation of a signal of a pattern bright part with a second predetermined standard value.

2. The pattern inspection apparatus according to claim 1, further comprising a focus sensor which detects a focus abnormal status of the illumination and imaging optics.

3. The pattern inspection apparatus according to claim 1, further comprising a vibration sensor which detects vibration of the stage for the plate to be inspected.

4. The pattern inspection apparatus according to claim 1, wherein the signal intensity profile analysis part compares the signal gradients of the horizontal and vertical directions with respect to the pattern edge part of the detected pattern data, and judges that vibration of the stage is generated, when a difference between the signal gradients is not less than the first predetermined standard value.

5. The pattern inspection apparatus according to claim 1, wherein the signal intensity profile analysis part compares the signal gradients of different diagonal directions of a pattern corner part of the detected pattern data, and judges that vibration of the stage is generated, when a difference between the signal gradients is not less than the predetermined standard value.

6. The pattern inspection apparatus according to claim 1, wherein the comparator stores the detected pattern data and the reference pattern data corresponding to the detected pattern data by the predetermined number of times, when the same abnormal status is detected by the predetermined number of times in a first predetermined time, and stops storage into the data memory with respect to the same abnormal status until a second predetermined time elapses.

* * * * *